United States Patent
Palermo

(10) Patent No.: US 7,101,703 B2
(45) Date of Patent: Sep. 5, 2006

(54) ELECTROFUSION MICROELECTRODE

(75) Inventor: Gianpiero D. Palermo, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 531 days.

(21) Appl. No.: 10/090,036

(22) Filed: Feb. 28, 2002

(65) Prior Publication Data

US 2002/0127723 A1 Sep. 12, 2002

Related U.S. Application Data

(60) Provisional application No. 60/274,378, filed on Mar. 9, 2001.

(51) Int. Cl.
*C12M 1/42* (2006.01)

(52) U.S. Cl. .............. 435/285.2; 435/286.5; 435/450; 435/461; 435/470

(58) Field of Classification Search ............. 435/285.2, 435/286.5, 450, 461, 470
See application file for complete search history.

(56) References Cited

U.S. PATENT DOCUMENTS

| | | | |
|---|---|---|---|
| 4,923,814 A | | 5/1990 | Marshall, III |
| 5,007,995 A | | 4/1991 | Takahashi et al. |
| 5,128,257 A | | 7/1992 | Baer |
| 5,185,922 A | * | 2/1993 | Pendley et al. ............... 29/825 |
| 5,304,486 A | | 4/1994 | Chang |
| 5,505,728 A | * | 4/1996 | Ellman et al. ................ 606/39 |
| 5,589,047 A | | 12/1996 | Coster et al. |
| 5,650,305 A | | 7/1997 | Hui et al. |
| 5,749,837 A | | 5/1998 | Palermo et al. |
| 5,827,736 A | | 10/1998 | Heller et al. |
| 5,859,327 A | | 1/1999 | Dev et al. |
| 5,983,131 A | | 11/1999 | Weaver et al. |
| 5,993,434 A | | 11/1999 | Dev et al. |
| 6,001,617 A | | 12/1999 | Raptis |
| 6,009,345 A | | 12/1999 | Hofmann |
| 6,077,261 A | | 6/2000 | Behl et al. |
| 6,150,148 A | | 11/2000 | Nanda et al. |
| 6,261,815 B1 | | 7/2001 | Meyer |
| 6,347,247 B1 | | 2/2002 | Dev et al. |
| 6,355,485 B1 | | 3/2002 | Jaroszeski et al. |
| 2002/0010414 A1 | | 1/2002 | Coston et al. |
| 2002/0019035 A1 | | 2/2002 | Tai et al. |

OTHER PUBLICATIONS

Webster's Ninth New Collegiate Dictionary, pp. 470–471.*
Stromburg et al., "Manipulating the Genetic Identity and Biochemical Surface Proteins of Individual Cells with Electric–Field–Induced Fusion," *PNAS* 97(1):7–11 (2000).
Stromburg et al., "Microfluidic Device for Combinatorial Fusion of Liposomes and Cells," *Anal. Chem.* 73:126–130 (2001).
Rae et al., "Instrument and Techniques Single–Cell Electroporation," *Pflügers Archiv–European Journal of PHysiology* (2001).
Haas, K. et al., "Single–Cell Electroporation for Gene Transfer In Vivo," *Neuron* 29:583–591 (2001).

* cited by examiner

*Primary Examiner*—James Ketter
(74) *Attorney, Agent, or Firm*—Nixon Peabody LLP

(57) ABSTRACT

The present invention is directed to an electrofusion microelectrode used in the alignment, manipulation, fusion, or electroporation of cells. This device is particularly useful for transplantation of cells and cellular components.

39 Claims, 3 Drawing Sheets

ELECTROFUSION MICROELECTRODE

This application claims the benefit U.S. Provisional Patent Application Ser. No. 60/274,378 filed Mar. 9, 2001.

BACKGROUND OF THE INVENTION

Electrofusion and electroporation of cells involves application of an electrical current to cells. In many instances, cells are aligned prior to applying a direct electrical current. Alignment may be done manually, for example, by aspiration or vacuum suction. Alignment may also be performed by applying an alternate electrical current. When alignment is done by applying alternate current, cell survival is drastically reduced. The present invention provides a tool having the dual capacity to manually align cells and deliver direct current to cells.

DESCRIPTION OF THE INVENTION

The present invention is directed to an electrofusion microelectrode which may be used in the alignment, manipulation, fusion or electroporation of cells including the transplantation of cells and cellular components. The electrofusion microelectrode comprises a tube encasing a filament which is an electric conductor. As used herein, "tube" is meant to encompass any hollow casing and may have any type of geometrical conformation. Thus, if desired, the walls of the tube may be angled. In a preferred embodiment, the tube is cylindrical. In an even more preferred embodiment, the tube is shaped as a holding pipette.

The tube as well as the conducting filament has both a medial and distal end. As used herein, the "medial end" of the tube or conducting filament is the end which contacts the cells and/or cellular components. The "distal end" of the tube or conducting filament is furthest away from the cells and/or cellular components and nearer a direct current power source.

The conducting filament may comprise any known conductor such as a metal, metal alloy or mixture of metals and/or metal alloys. Certain carbon allotropes may also be used to form the conducting filament. Examples of metal conductors which may be used as a conducting filament include but are not limited to, aluminum, copper, silver, gold, titanium, platinum, and tungsten. An example of a carbon allotrope which may be used as a conducting filament in the electrofusion microelectrode is graphite. In a preferred embodiment, the metal filament is made of tungsten or tungsten alloy.

Figure 1:
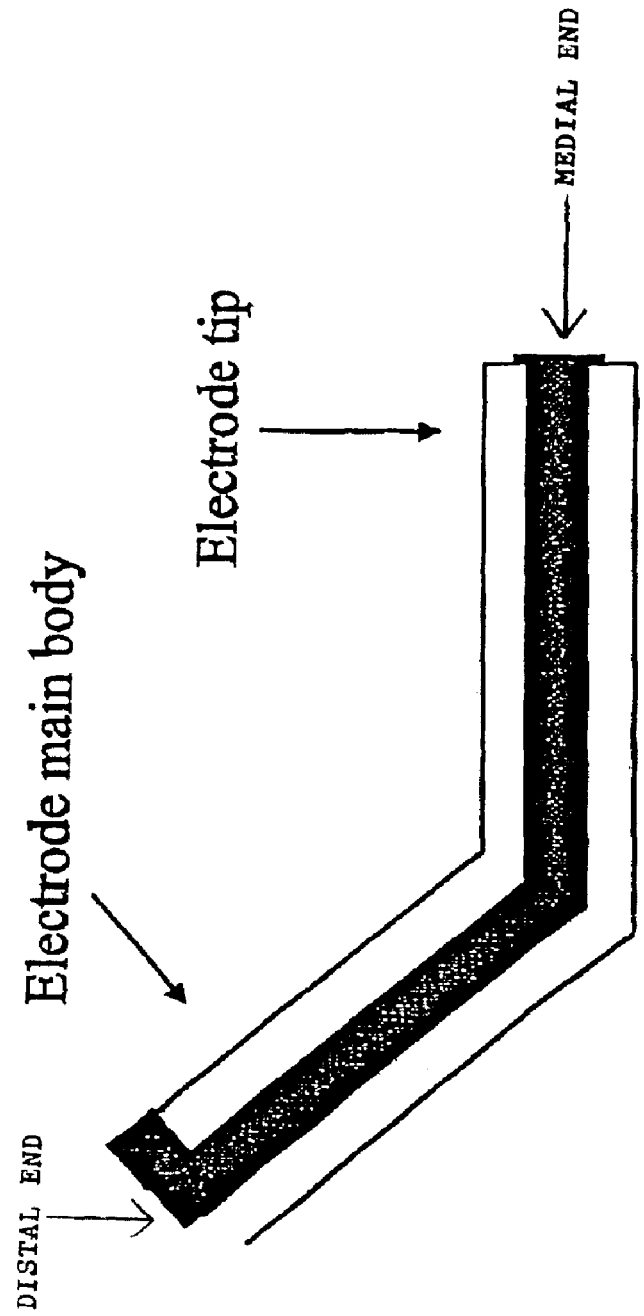
FIG. 1 is an illustration of one embodiment of the electrofusion microelectrode. In this embodiment, the first end of the tube is sealed.
Figure 2:
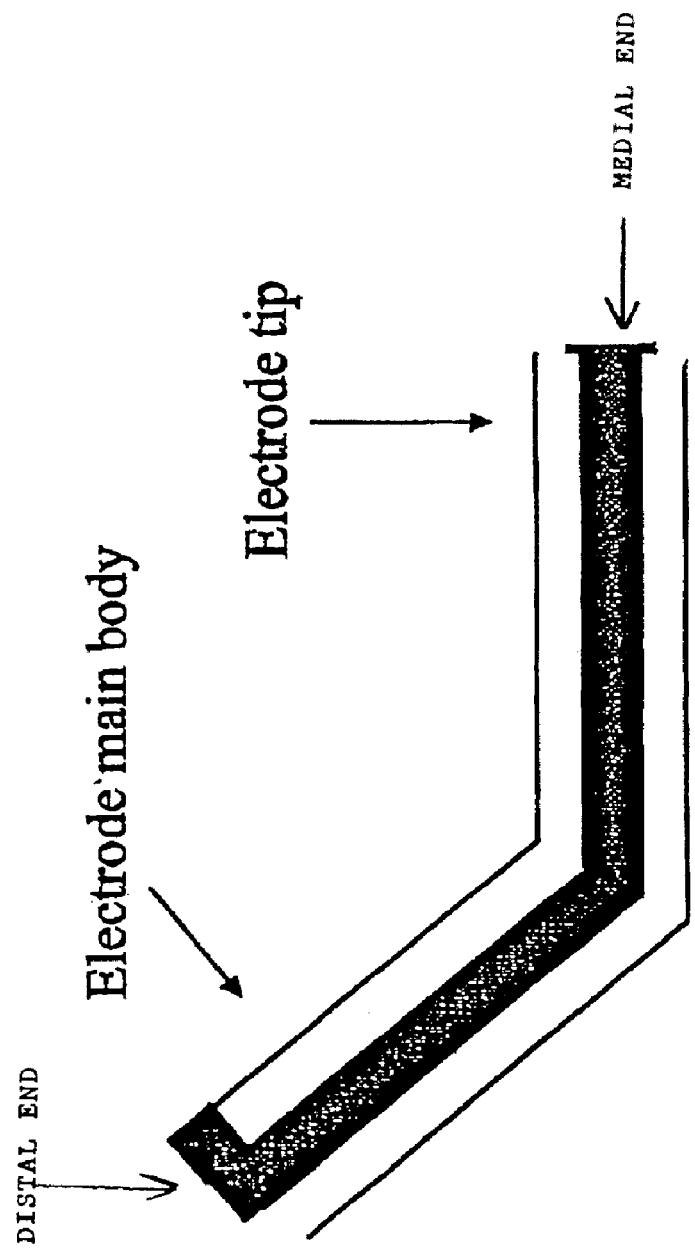
FIG. 2 is an illustration of another embodiment of the electrofusion microelectrode. In this embodiment, the first end of the tube is open.

In one embodiment of the invention, one end of the filament is flattened at the tip of one end of the tube and the tube is sealed at this end (medial end). In an alternative embodiment, the electrofusion microelectrode has an internal opening surrounding the filament. The internal opening is useful to allow aspiration or vacuum suctioning of cells such as used with a standard holding pipette. In this embodiment, the end of the tube which is in contact with the cells or cellular components, i.e., the medial end, is open. In FIG. 1, the first (medial) end of the tube where the first (medial) end of the filament protrudes is sealed. FIG. 2 shows an alternative embodiment where the first end of the tube is open.

The tube portion of the electrofusion microelectrode may be made of any number of materials such as glass, plastic, PVC, ceramic, metal, etc. In a preferred embodiment, the tube portion is made of glass. In a more preferred embodiment, the tube portion is made from a borosilicate glass capillary tube, pulled and forged as a holding pipette.

The length and diameter of the electrofusion microelectrode may vary according to the type of cells and type of manipulation for which the tool is used. For example, when used for nuclear transplantation of mammalian cells, a tube diameter in the range of from about 15 to about 25 µm is useful. When used for mammalian cell fusion, a tube diameter in the range of from about 60 to about 100 µm may be used. Thus, in one embodiment, the outer diameter of the tube may be about 0.97 mm while the inner diameter of the tube may be about 0.69 mm. In this embodiment, the tube is quite thin walled, having a thickness of only about 0.28 mm. The diameter of the conducting filament may be anywhere in the range of from about 7 to about 20 µm. The distal end of the conducing filament is preferably thicker than the medial end so that connection to a power source is conveniently achieved.

The length of the microelectrode can of course, vary. A length of about 78 mm is convenient for most manipulations. Typically, there is a bend in the tube approximately 1 mm or so from the medial end.

With reference to FIG. 1, one embodiment of the invention is illustrated therein and it will be seen to include an electrode main body and an electrode tip. As illustrated in FIG. 1, a conductor filament extends throughout the tube (electrode main body). Both the tube and the filament have a first (medial) and a second (distal) end. A first (medial) end of a filament protrudes through a first (medial) end of the tube and is flattened at the tip of the first (medial) end of the tube. In FIG. 1, the medial ends make up the electrode tip. A second (distal) end of the filament protrudes through a second (distal) end of the tube and is configured to both allow the filament to remain relatively fixed within the tube and to allow connection to a power source. The medial end of the tube may be open, or closed (sealed).

Figure 3:
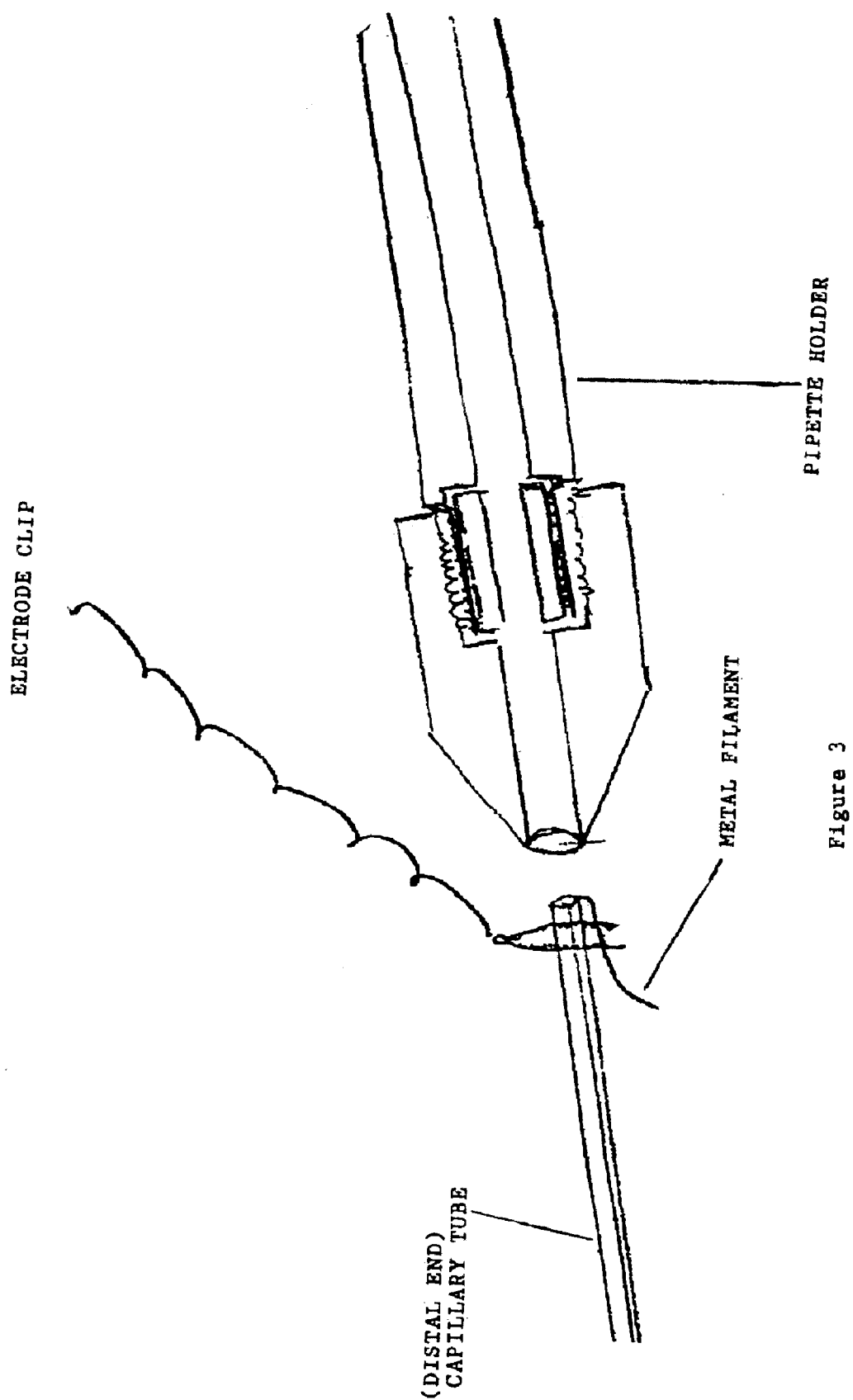
FIG. 3 is an illustration depicting the electrofusion microelectrode connected to a power source via an electrode clip. In this illustration, the microfilament protrudes from the tube at the distal end and is bent or looped. The electrode clip is clamped on the distal end of the tube and also contacts the bent portion or loop of the conducting filament. Suction means via a pipette holder is also depicted in this figure and may be connected to the distal end of the electrofusion microelectrode.

There are many possible configurations for the distal, protruding end of the filament. In one embodiment, the distal end of the filament may be bent or looped towards the outer wall of the tube or wrapped around the outer wall of the tube in order to have the filament remain relatively fixed within the tube. Conveniently, an electrode clip or the like may be clamped around the tube as well as the looped, bent, or wrapped portion of the distal end of the filament. This embodiment of the invention is depicted in FIG. 3.

In another embodiment of the invention, the medial end of the conducting filament does not protrude from the medial end of the tube. The inner walls of the tube are painted with a liquid form of an electric conductor from a place where the filament no longer extends to the medial end of the tube and the paint extends to the outside (lateral) edge of the medial end of the tube. In this embodiment, the distal ends of the filament and tube are as described above. Again, the medial end of the tube may be open or closed (sealed).

In yet another embodiment of the invention, rather than using a conducting filament, the inner portion of the tube is painted with a liquid form of an electric conductor. Examples include liquid aluminum, copper, silver, gold, titanium, platinum, tungsten, and alloys and mixtures thereof. Thus, at least a portion of the inner walls are painted with a liquid electric conductor and the painted area extends continually from the medial end of the tube to the distal end of the tube. The medial end of the tube may be opened or sealed. The liquid conductor is also painted on at least a portion of the outer (lateral) edge of both the medial and distal ends of the tube. Further, a portion of the liquid conductor is applied to the outside wall of the tube at the distal end so that connection to a direct current power source may be achieved. For example, an electrode clip may be clamped to the tube, contacting that portion of the distal end of the outer wall of the tube which is painted with the liquid conductor.

The electrofusion microelectrode is preferably mounted on a tool holder where it can be controlled by a micromanipulator. Preferably, the micromanipulator is used under inverted microscopy. Examples of micromanipulators which may be used with the subject electrofusion microelectrode include but are not limited to, the MM188 and MM109 manufactured by Narishigie Co., LTD, Tokyo, Japan. Preferably, the electrofusion microelectrode is used as a set of two: the distal end of the conducting filament of one electrofusion microelectrode being connected to the positive terminal of a direct current power source, and the distal end of the conducting filament of a second subject electrofusion microelectrode being connected to the negative terminal of a direct current power source. The power source should be able to deliver at least 1 kilovolt per centimeter, direct current. Examples of power sources that may be used with the subject microelectrode include the BTX Electro Cell Manipulator 200 or 2001 (BTX Inc., San Diego, Calif.).

The subject tool(s) may be used to perform the techniques of electrofusion/electroporation by manually aligning and/or or micromanipulating the cells using microelectrode motion. Alternatively, if the medial end of the tool(s) is open, cells may be manually aligned using aspiration or vacuum suction. Of course, a combination of microelectrode motion and aspiration or suction may be used to micromanipulate and/or align cells. After aligning cells, direct current may be applied via the subject microelectrode(s). Since cells are aligned manually, the use of alternate current for alignment is avoided, significantly improving cell survival. Since cell survival is drastically improved, much lower cell numbers may be used in each manipulation.

The present invention therefore provides methods of manipulating cells using the subject electrofusion microelectrode. Such methods include for example, cell transplantation, electrofusion of cells, electroporation of cells, and nuclear transplantation. Thus, the present invention provides a method of transplanting mammalian cells which comprises micromanipulating the cells with two electrofusion microelectrodes and delivering a direct current to the manipulated cells. The subject electrofusion microelectrodes for use in the method of transplantation of mammalian cells, may have any of the alternate embodiments hereinbefore described.

The present invention also provides a method of electrofusion of cells. The method comprises aligning cells between two electrofusion microelectrodes and delivering a direct current to the aligned cells. Again, the subject electrofusion microelectrodes for use in the method of electrofusion of cells, may have any of the alternate embodiments hereinbefore described.

Also provided by the present invention is a method of electroporation of cells. The method comprises manipulating cells with two electrofusion microelectrodes and delivering a direct current to the manipulated cells. The subject electrofusion microelectrodes for use in the method of electroporation may have any of the alternate embodiments hereinbefore described.

A method of nuclear transplantation is also provided by the present invention. The method comprises removing a nucleus from a first oocyte and transplanting the nucleus into the perivitelline space of a second, previously enucleated oocyte, and then integrating the transplanted nucleus of the first oocyte with the cytoplasm of the second oocyte. Transplantation and integration is performed using the subject electrofusion microelectrodes and integration is achieved by delivering a direct current to the nucleus and cytoplasm. The subject electrofusion microelectrodes for use in the method of nuclear transplantation may have any of the alternate embodiments hereinbefore described.

EXAMPLE I

A capillary tube, 78 mm in length, and having an outer diameter of 0.97 mm and an inner diameter of 0.69 mm (Drummond Scientific, Boomall, Pa.), is pulled on a horizontal microelectrode puller (micropuller) (Campden Inc., LTD., London) approximately 60 to 100 µm at a location of 10–15 mm from one end (medial end). The tube is cut and fine polished on a microforge (Narishige Co., LTD, Tokyo, Japan) to obtain a final outer diameter of 60 µm and an inner diameter of 20 µm. A platinum filament having a thickness of about 20 to 40 µm (available from a fine jeweler) is inserted into the distal end of the pipette under a sterile microscope with a magnification of 6–15× or a magnifying lens of at least 6×. The medial end of the conducting filament is placed flush against the tip of the medial end of the pipette. The distal end of the filament is of a length longer than the pipette so that that it exits the distal end of the pipette by a length of at least 10 mm. This portion of the filament which exits the distal end of the pipette is bent towards the outside wall of the distal end of the pipette, making a bend or a loop to secure the filament in place within the pipette and to allow connection to a power source by means of an electrode clip. An electrode clip may be attached to the tube, ensuring that contact with the protruding portion of the distal end of the filament is made (FIG. 3). The electrode clip may be connected to a direct current power source such as the BTX Electro Cell Manipulator 200 or 2001 (San Diego, Calif.).

EXAMPLE II

Nuclear Transplantation for Immature Mammalian Oocytes

Germinal vesicle (GV) stage oocytes are retrieved by puncturing follicles of unstimulated ovaries of B6D2F1 female mice. A karyoplast is then removed by micromanipulation using one or more of the subject electrofusion microelctrodes in a medium supplemented with cytochalasin B. One karyoplast is subsequently introduced into the perivitelline space of a previously enucleated immature oocyte. Each grafted oocyte is then positioned between two of the subject electrofusion microelectrodes and exposed to a single or double 1.0 kV/cm, 50–99 μm direct current fusion pulse(s). Thirty to 60 minutes later, the oocytes are examined for sign of fusion. The restored oocytes are then placed in culture and assessed for maturation. Oocytes which have extruded a first polar body may be fixed and stained with Giemsa for chromosome analysis. As controls, approximately one third of oocytes are not subjected to any manipulation, but are merely cultured in the same media and exposed to same reagents.

EXAMPLE III

Germinal Vesicle Transplantation

Germinal vesicle (GV) stage oocytes are retrieved by puncturing follicles of unstimulated ovaries of B6D2F1 female mice. Metaphase II (MII) oocytes are collected 15 hours after hCG injection of PMSG stimulated females. Karyoplasts are then removed from GV oocytes using one or more subject electrofusion microelectrodes, in a medium supplemented with cytochalsin B. MII oocytes are enucleated by removing the "hub" area where the metaphase spindle is located, together with the first polar body using one or more of the subject electrofusion microelectrodes. A GV karyoplast is subsequently introduced into the perivitelline space of either a previously enucleated immature (GV) or a mature (MII) oocyte. Each of these manipulated oocytes is then positioned between two of the subject electrofusion microelectrodes and exposed to a single or double 1.0 kV/cm, 50–99 μm direct current fusion pulse(s) for electrofusion. The oocytes that show signs of fusion 30 to 60 minutes later are then placed in culture for 12 hours, to allow nuclear maturation. Oocytes which extrude the first polar body may be fixed and stained with Giemsa for chromosome analysis.

What is claimed:

1. An electrofusion microelectrode for manipulating cells or cellular components which comprises a conducting filament encased in a tube, wherein a first (medial) end of the filament has a tip which protrudes from a first (medial) end of the tube, the first (medial) end of the filament being broadened at the tip, and wherein a second (distal) end of the filament protrudes from a second (distal) end of the tube and wherein the second (distal) end of the filament is configured to allow the filament to remain relatively fixed within the tube and to allow connection to a direct current power source.

2. An electrofusion microelectrode which comprises a tube, wherein at least a portion of the inner walls are painted with a liquid electric conductor and wherein the painted electric conductor extends continually from a first (medial) end of the tube to a second (distal) end of the tube, wherein the liquid electric conductor is further painted on a least a portion of the outer (lateral) edge of both the first (medial) and second (distal) ends of the tube, wherein an area on the outer wall of the tube at the second (distal) end is painted with the electric conductor and wherein the painted area of the outer wall of the tube at the second (distal) end meets the painted area of the outer (lateral) edge of the second (distal) end of the tube, and wherein the distal end of the tube is connectable to a direct current power source.

3. An electrofusion microelectrode which comprises a conducting filament encased in a tube, wherein a first (medial) end of the filament extends toward a first (medial) end of the tube, and wherein a second (distal) end of the conducting filament protrudes from a second (distal) end of the tube, wherein at least a portion of the inner walls near the first (medial) end of the tube is painted with an electric conductor in an area where the conducting filament does not extend, and wherein the second (distal) end of the conducting filament is configured to allow the filament to remain fixed within the tube and to allow connection to a direct current power source.

4. The electrofusion microelectrode of any of claims 1–3 wherein the tube is shaped as a holding pipette.

5. The electrofusion microelectrode of any of claims 1–3 wherein the first (medial) end of the tube is sealed.

6. The electrofusion microelectrode of any of claims 1–3 wherein the first (medial) end of the tube is open.

7. The electrofusion microelectrode of any of claims 1–3 wherein the tube is made of plastic, PVC, ceramic, or metal.

8. The electrofusion microelectrode of any of claims 1–3 wherein the tube is made of glass.

9. The electrofusion microelectrode of claims 1 or 3 wherein the conducting filament is made of a metal, metal alloy, or mixture of metals.

10. The electrofusion microelectrode of claim 9 wherein the metal or metal alloy is at least one of aluminum, copper, silver, gold, titanium, platinum, or tungsten.

11. The electrofusion microelectrode of any of claims 1–3 wherein the second (distal) end of the tube is connectable to a vacuum or hand held aspirator.

12. The electrofusion microelectrode of claim 11 wherein the hand held aspirator is a pipette holder.

13. The electrofusion microelectrode of any of claims 1–3 further comprising:
a tool holder on which the electrofusion microelectrode is mounted.

14. The electrofusion microelectrode of claim 13 further comprising:
a micromanipulator which controls the tool holder.

15. The electrofusion microelectrode of claims 1 or 3, wherein the second (distal) end of the conducting filament is configured by being bent or looped towards the outer wall of the tube or being wrapped around the outer wall of the tube.

16. An electrofusion microelectrode for manipulating cells or components which comprises a conducting filament in a tube, wherein a first (medial) end of the filament protrudes from a first (medial) end of the tube, the first (medial) end of the tube being open, and wherein a second (distal) end of the filament protrudes from a second (distal) end of the tube, wherein the second (distal) end of the filament is configured to allow the filament to remain relatively fixed within the tube and to allow connection to a direct current power source.

17. The electrofusion microelectrode of claim 16, wherein the tube is shaped as a holding pipette.

18. The electrofusion microelectrode of claim 17, wherein the tube is made of plastic, PVC, ceramic, or metal.

19. The electrofusion microelectrode of claim 17, wherein the tube is made of glass.

20. The electrofusion microelectrode of claim 17, wherein the conducting filament is made of a metal, metal alloy, or a mixture of metals.

21. The electrofusion microelectrode of claim 20, wherein the metal or metal alloy is at least one of aluminum, copper, silver, gold, titanium, platinum, or tungsten.

22. The electrofusion microelectrode of claim 17, wherein the second (distal) end of the tube is connectable to a vacuum or hand held aspirator.

23. The electrofusion microelectrode of claim 22, wherein the hand held aspirator is a pipette holder.

24. The electrofusion microelectrode of claim 17 further comprising:
a tool holder on which the electrofusion microelectrode is mounted.

25. The electrofusion microelectrode of claim 17 further comprising:

a micromanipulator which controls the tool holder.

26. The electrofusion microelectrode of claim 17, wherein the second (distal) end of the conducting filament is configured by being bent or looped towards the outer wall of the tube or being wrapped around the outer wall of the tube.

27. A system for manipulating cells or cellular components comprising:

a direct current power source comprising a positive and negative terminal;

first and second electrofusion microelectrodes, each comprising a conducting filament in a tube, wherein a first (medial) end of the filament protrudes from a first (medial) end of the tube, the first (medial) end of the tube being open, and wherein a second (distal) end of the filament protrudes from a second (distal) end of the tube, wherein the second (distal) end of the filament is configured to allow the filament to remain relatively fixed within the tube, wherein the second (distal) end of the filament from the first electrofusion microelectrode is connected to the positive terminal of the direct current power source and the second (distal) end of the filament from the second electrofusion microelectrode is connected to the negative terminal of the direct current power source.

28. The system of claim 27, wherein the direct current power source is capable of delivering at least 1 kilovolt per centimeter of direct current.

29. The system of claim 28, wherein each of the tubes of the first and second electrofusion microelectrodes is shaped as a holding pipette.

30. The system of claim 28, wherein each of the tubes of the first and second electrofusion microelectrodes is made of plastic, PVC, ceramic, or metal.

31. The system of claim 28, wherein each of the tubes of the first and second electrofusion microelectrodes is made of glass.

32. The system of claim 28, wherein each of the conducting filaments of the first and second electrofusion microelectrodes is made of a metal, metal alloy, or a mixture of metals.

33. The system of claim 32, wherein the metal or metal alloy is at least one of aluminum, copper, silver, gold, titanium, platinum, or tungsten.

34. The system of claim 28, wherein each of the second (distal) ends of the tube of the first and second electrofusion microelectrodes is connectable to a vacuum or hand held aspirator.

35. The system of claim 34, wherein the hand held aspirator is a pipette holder.

36. The system of claim 35 further comprising:

an aspirator or suction device connected to each of the second (distal) ends of the tube of the first and second electrofusion microelectrodes.

37. The system of claim 28 further comprising:

a first and second tool holder on which each of the first and second electrofusion microelectrodes is mounted.

38. The system of claim 28 further comprising:

a first and second micromanipulator each of which controls the tool holder.

39. The system of claim 28, wherein each of the second (distal) ends of the conducting filament of the first and second electrofusion microelectrodes is configured by being bent or looped towards the outer wall of the tube or being wrapped around the outer wall of the tube.

* * * * *

UNITED STATES PATENT AND TRADEMARK OFFICE
CERTIFICATE OF CORRECTION

PATENT NO. : 7,101,703 B2
APPLICATION NO. : 10/090036
DATED : September 5, 2006
INVENTOR(S) : Gianpiero D. Palermo It is certified that error appears in the above-identified patent and that said Letters Patent is hereby corrected as shown below:

Col. 6 at claim 18, first line, delete "17" and insert --16-- in its place.

Col. 6 at claim 19, first line, delete "17" and insert --16-- in its place.

Col. 6 at claim 20, first line, delete "17" and insert --16-- in its place.

Col. 6 at claim 22, first line, delete "17" and insert --16-- in its place.

Col. 6 at claim 24, first line, delete "17" and insert --16-- in its place.

Col. 7 at claim 25, first line, delete "17" and insert --16-- in its place.

Col. 7 at claim 26, first line, delete "17" and insert --16-- in its place.

Col. 7 at claim 29, first line, delete "28" and insert --27-- in its place.

Col. 7 at claim 30, first line, delete "28" and insert --27-- in its place.

Col. 8 at claim 31, first line, delete "28" and insert --27-- in its place.

Col. 8 at claim 32, first line, delete "28" and insert --27-- in its place.

Col. 8 at claim 34, first line, delete "28" and insert --27-- in its place.

Col. 8 at claim 36, first line, delete "35" and insert --27-- in its place.

Col. 8 at claim 37, first line, delete "28" and insert --27-- in its place.

Col. 8 at claim 38, first line, delete "28" and insert --27-- in its place.

UNITED STATES PATENT AND TRADEMARK OFFICE
CERTIFICATE OF CORRECTION

PATENT NO. : 7,101,703 B2
APPLICATION NO. : 10/090036
DATED : September 5, 2006
INVENTOR(S) : Gianpiero D. Palermo It is certified that error appears in the above-identified patent and that said Letters Patent is hereby corrected as shown below:

Col. 8 at claim 39, first line, delete "28" and insert --27-- in its place.

Signed and Sealed this

Tenth Day of April, 2007

JON W. DUDAS
*Director of the United States Patent and Trademark Office*